(12) United States Patent
Goldenberg

(10) Patent No.: US 7,608,049 B2
(45) Date of Patent: Oct. 27, 2009

(54) BIOPSY NEEDLE

(76) Inventor: Alec S. Goldenberg, 157 E. 32nd St., 2nd Floor, New York, NY (US) 10016

(*) Notice: Subject to any disclaimer, the term of this patent is extended or adjusted under 35 U.S.C. 154(b) by 0 days.

(21) Appl. No.: 12/042,314

(22) Filed: Mar. 4, 2008

(65) Prior Publication Data

US 2009/0227895 A1 Sep. 10, 2009

(51) Int. Cl.
*A61B 10/00* (2006.01)
*A61B 17/32* (2006.01)
(52) U.S. Cl. .............. 600/564; 600/562; 600/567; 606/167; 606/170
(58) Field of Classification Search ............... 600/562, 600/564, 566–568; 606/167, 170
See application file for complete search history.

(56) References Cited

U.S. PATENT DOCUMENTS

| 3,605,721 | A | 9/1971 | Hallac |
| 4,262,676 | A | 4/1981 | Jamshidi |
| 5,074,311 | A | 12/1991 | Hasson |
| 5,490,859 | A * | 2/1996 | Mische et al. ............... 606/170 |
| 5,522,398 | A | 6/1996 | Goldenberg et al. |
| 6,015,391 | A * | 1/2000 | Rishton et al. .............. 600/567 |
| 7,338,456 | B2 | 3/2008 | Goldenberg |
| 2005/0054948 | A1* | 3/2005 | Goldenberg ............... 600/567 |
| 2007/0265548 | A1 | 11/2007 | Goldenberg |

\* cited by examiner

*Primary Examiner*—Max Hindenburg
*Assistant Examiner*—Emily M Lloyd
(74) *Attorney, Agent, or Firm*—Leason Ellis LLP

(57) ABSTRACT

According to one embodiment, a biopsy needle for removal of tissue from a patient includes an outer tube having a distal end and an inner tube disposed within the outer tube. The needle includes a capturing mechanism that has a variable diameter for capturing a tissue specimen. The capturing mechanism includes a distal first end that is fixed relative to the distal end of the outer tube and an opposing proximal end that is attached to the inner tube. The inner tube is free to move longitudinally within and relative to the outer tube, whereby longitudinal movement of the inner tube causes activation of the capturing mechanism resulting in the closing and opening, respectively, of the capturing mechanism to capture and release the specimen, respectively.

23 Claims, 9 Drawing Sheets

BIOPSY NEEDLE

TECHNICAL FIELD

This invention relates generally to a surgical instrument, known variously as a biopsy needle or biopsy cannula that is used to gather specimens from the bone marrow or soft tissues of living persons or animals for pathological study. More specifically, the invention relates to a biopsy needle having an improved structure for severing a tissue sample and/or retaining the tissue sample within the needle.

BACKGROUND

For various medical reasons, such as evaluating the histology and/or pathology of a tissue, it is often necessary for a physician to obtain a sample of a patient's body tissue. In particular, bone marrow is frequently retrieved to study its cellularity and potential infiltration with abnormal cells. The currently available procedures and instruments used for obtaining bone marrow biopsy samples, while not overly complex, almost universally result in excessive patient discomfort and often recover inadequate quantities of biopsy material which sometimes is distorted and/or difficult to interpret. In the standard bone marrow procurement protocol, using currently available instruments, (such as those disclosed in U.S. Pat. No. 4,262,676 to Khosrow Jainshidi), the patient is prepared with a suitable local anesthetic at the posterior superior iliac crest/spine. Then, a relatively narrow needle is inserted to obtain an aspirate of liquid bone marrow material to make slides for examination of cellular morphology and to evaluate the surface immunophenotype of the bone marrow cells with flow cytometry. This portion of the procedure, referred to as the bone marrow aspiration, is generally relatively less painful than the bone marrow biopsy procedure using a conventional biopsy needle. Using newer bone marrow biopsy needles which actively capture specimens, and minimize manipulation of the needle after insertion, the aspirate procedure appears to be more painful than the biopsy procedure.

After the aspirate is obtained, if necessary, a biopsy of the bone marrow is taken. A significantly wider bore needle having an inner diameter that will accommodate a suitable marrow sample is prepared with an inner stylet that extends beyond the distal end of the outer needle. The stylet's distal end may be cut at an angle, with the leading edge sufficiently sharp to pierce tissue and bone. With the stylet in place within the outer needle, the needle is pushed through the outer layers of skin and subcutaneous tissue until the needle tip reaches the surface of the cortical bone. The needle and stylet are then pushed into and through the cortical layer until the tip has penetrated into the bone marrow space.

The stylet is then removed from the proximal end of the needle, which opens up the core of the needle to accommodate entry of bone marrow material for collection and retrieval. The needle is then usually advanced another 1 to 2 centimeters at minimum with a slight twisting motion. Often, the distal end of the needle will also be provided with an angled cut and sharpened leading edge or scalloped serrations to facilitate cutting and coring the tissue. By providing a slight twisting motion as the needle is advanced, usually with no more than quarter or half turns, an appropriate sample is cored from the marrow tissue and enters the inner passage of the marrow needle.

At this point, the marrow biopsy sample is ready to be removed from the patient, although it is important that the biopsy remain within the needle as the needle is withdrawn to ensure recovery of the specimen. If the biopsy becomes dislodged and falls through the distal end of the biopsy needle, the specimen is irretrievably lost. The procedure is then unsuccessful and must be repeated from the beginning.

Various methods have been utilized by physicians to try to prevent the biopsy specimen from dislodging from the needle. For example, after the needle has entered the bone and fully cored a sample from the marrow, some physicians will pull the biopsy needle back a few millimeters and then advance it a few millimeters at a different angle than the first insertion. This theoretically will "cut" the biopsy piece at the tip of the needle. Other physicians attempt to dislodge or disrupt the connection between the specimen and the bone by making multiple complete clockwise and counterclockwise rotations of the biopsy needle while within the bone. Some physicians even hit the proximal end of the biopsy needle at its handle in an attempt to mechanically disrupt the connection between the specimen and the additional bone.

As can be plainly realized, these manipulations at the end of the procedure, attempts at ensuring that the specimen remains within the needle, can often produce substantial discomfort and anxiety to the patient. Sometimes when the bone marrow is very soft, as in patients with osteoporosis, almost all of these attempts are futile because the bone structure is so fragile. Conversely, sometimes when the bone marrow is very fibrotic, which occurs in patients with myelofibrotic diseases or in AIDS patients, it is difficult to dislodge the core biopsy, since the bone marrow itself is reinforced by the surrounding tissue. In those cases, the cored biopsy often remains attached to the bone and is not successfully recovered.

Other attempts at designing a more efficient and successful biopsy needle have met with little or no success, for various reasons, including the complexity of the devices. For example, U.S. Pat. No. 3,605,721 to Hallac, discloses a biopsy needle in which an inner tube has a weakened portion represented by strips extending between distal and proximal portions of the inner tube. The distal portion of the inner tube is adhered to an outer tube and will not rotate. Once a biopsy has entered the needle, the proximal portion of the inner tube is rotated, causing the strips to twist together and eventually break off. This twisting motion tends to twist the strips to the tube's center, thus hopefully keeping the biopsy piece proximal of the twisted and broken strips for later removal. This particular biopsy needle is only a disposable device, since the strips are broken or irreversibly warped by deformation during the twisting process. Another disadvantage is the lack of control over the twisting motions or the breakage of the strips. Essentially, the operator is left to twist the inner tube until resistance to that twisting is lost, indicating that the strips have severed. There is also no way of releasing the device's grip on tissue during the procedure, should any problems arise.

U.S. Pat. No. 5,074,311 to Hasson discloses a biopsy device that includes a pair of inner jaws that can be actuated within the outer needle to "bite off" any biopsy piece that has entered the needle. The disadvantages of this device include multiple small mechanical linkages and parts including pivot pins, which are extremely difficult and expensive to assemble and maintain, in addition to the greatly increased chance of mechanical failure resulting in failure to retrieve an adequate specimen.

U.S. Pat. No. 5,522,398, to Goldenberg et al., discloses a bone marrow biopsy needle; however, the patent teaches that an inner diameter B at the distal tip of the needle (as shown in FIG. 4 thereof) is substantially equal to an inner diameter C of the inner tube (as shown in FIG. 3C) so that there will be no ridge or lip within the instrument to impede tissue entering the inner lumen of the needle. However, observations over time of the performance of needles constructed in this manner indicates that such a relationship may impede specimen transit into and through the needle, and that a virtual obstruction phenomena may develop as a result of the above relationship between the two inner diameters. Compromise of specimen transit into the needle results in an inability of the specimen to move forward into the lumen of the needle. In addition, as the needle penetrates tissue, external pressures, especially those produced by dense bone, could deform or change the diameter at the needle tip (inner diameter B) or might transmit a force through the wall of the needle, marginally decreasing the diameter of the inner tube or snare (inner diameter C). These changes could dynamically alter the relationship between the inner diameters and cause a virtual obstruction, impeding specimen transit and making it difficult for the specimen to move forward into the needle.

Many soft tissue biopsy needles incorporate a recess in a central stylet/shaft into which the tissue prolapses and over which an outer tube passes in order to sever and capture specimens. However, since the recess can never encompass the full diameter of the lumen of the needle, such designs, by definition, can never recover full cores of tissue for analysis, limiting their ability to recover the most representative tissue samples. Also, the tendency for the tissue to prolapse into the recess will depend on the deformability characteristics of the tissue. Sclerotic/fibrotic components of soft tissue may make the material minimally deformable, therefore limiting the procedure's ability to capture adequate tissue samples for analysis. Needles which do not have recessed shafts and collect specimens by boring a full core of tissue have been limited by their ability to secure, sever and capture the tissue within the lumen of the needle for efficient recovery. Capturing mechanisms such as snare coils, as disclosed in U.S. Pat. No. 5,522,398, to Goldenberg et al., (incorporated herein by reference in its entirety) that sit within the lumen of needles can be incorporated into needles designed for soft tissue biopsy. Although a snare coil captures specimens by reducing its diameter, to adequately sever and recover a soft tissue specimen, which is more compressible then bony materials, the snare coil must be designed to reduce its diameter to a minimum. However, capturing coils whose geometries are reduced by alternative activation mechanics may be more efficient in reducing their diameters and displacing their capturing coils more efficiently towards the central axis of the lumen of the needle. Such internal capturing coils may find more applicability in more deformable materials such as softer tissues that require sampling for pathologic evaluation.

SUMMARY

According to one embodiment, a biopsy needle for removal of tissue from a patient includes an outer tube having a distal end and an inner tube disposed within said outer tube. The needle includes a capturing mechanism that has a variable diameter for capturing a tissue specimen. The capturing mechanism includes a distal first end that is fixed relative to the distal end of the outer tube and an opposing proximal end that is attached to the inner tube. The inner tube is free to move longitudinally within and relative to the outer tube, whereby longitudinal movement of the inner tube causes activation of the capturing mechanism resulting in the closing and opening, respectively, of the capturing mechanism to capture and release the specimen, respectively.

According to one embodiment, a biopsy needle for removal of tissue from a patient includes an outer tube; an inner tube disposed within and movable in a longitudinal direction relative to the outer tube; and a specimen capturing member that has a variable diameter for capturing a tissue specimen. The capturing member is coupled at a first end to a fixed structure that is different from the inner tube which moves longitudinally. The specimen capturing member also is coupled at a second end to the inner tube. Longitudinal movement of the inner tube relative to the outer tube causes activation of the specimen capturing member resulting in the closing and opening, respectively, of the specimen capturing member to capture and release the specimen, respectively.

In another embodiment, a method for removal of tissue from a patient includes the steps of: providing a biopsy needle including an outer tube having a distal end and an inner tube disposed within the outer tube. The inner tube is free to move longitudinally within the outer tube. The needle further includes a capturing mechanism that has a variable diameter for capturing a tissue specimen. The capturing mechanism including a distal first end that is fixed, indirectly or directly, to the distal end of the outer tube and an opposing proximal end that is attached to the inner tube. The method further includes the step of longitudinally moving the inner tube in one direction relative to the outer tube to activate the capturing mechanism resulting in the closing and opening, respectively, of the capturing mechanism to capture and release the specimen, respectively.

BRIEF DESCRIPTION OF THE DRAWINGS

Other objects, advantages and embodiments than those described above will become apparent to those skilled in the art upon reading the following detailed description of the preferred embodiments in conjunction with a review of the appended drawings, in which.

DETAILED DESCRIPTION OF THE PREFERRED EMBODIMENTS

Figure 1:
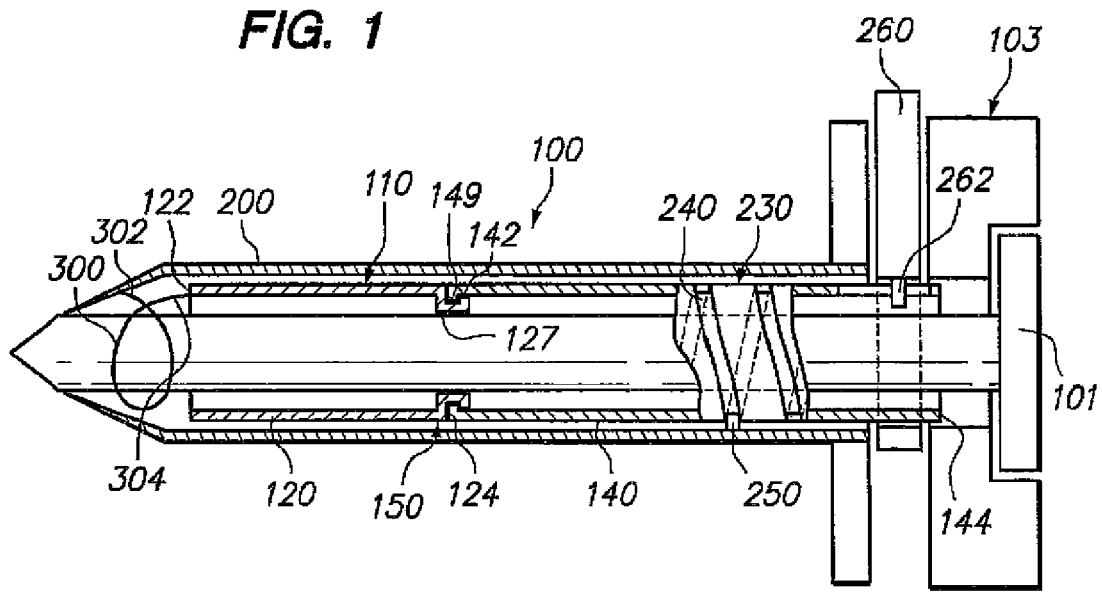
FIG. 1 is a cross-sectional view of a section of a biopsy needle in accordance with a first embodiment of the present invention.

Referring now to FIG. 1, a section of a biopsy needle 100 is illustrated according to one embodiment of the present invention. It will be appreciated that a number of components of the biopsy needle 100 are not shown for ease of illustration and to more clearly illustrate the features of the present invention. However, in order to show some of the basic components of the needle 100, a stylet 101 and a handle assembly 103 are shown in FIG. 1. However, details of these and other components of the needle 100 are illustrated in commonly owned U.S. Pat. Nos. 7,338,456 and 7,384,400, each of which is hereby incorporated by reference in its entirety.

The biopsy needle 100 is formed primarily of three components, namely, an inner tube or cannula 110, an outer tube or cannula 200 and a specimen capturing mechanism 300. It will be understood that the handle assembly actuates the capturing mechanism 300 within the outer cannula 200 without requiring the operator to move the outer cannula 200 relative to the patient (not shown) by allowing the proximal portion of the inner tube to rotate relative to the outer tube causing the inner tube to be translated longitudinally along the axis of the needle, thereby activating the capturing mechanism.

In contrast to Applicant's previous other needle designs, the inner tube 110 is constructed so that its motion relative to the outer tube is longitudinal instead of being designed to rotate relative to the outer tube 200, as specified in the Applicant's previous snarecoil needle designs. The inner tube is moved longitudinally relative to the outer tube since in this needle, longitudinal motion of the inner tube is required for longitudinal displacement of the capturing mechanism which results in activation of the mechanism as opposed to the rotational motion between the inner tube 110 and outer tube 200 that was required for capturing mechanism activation in Applicant's prior needle designs.

In order to generate translational inner tube motion, the inner tube 110 of FIG. 1 is formed of a first part or component 120 and a second part or component 140. The first part 120 represents a more distal component, whereas, the second part 140 represents a more proximal part. In particular, the first part 120 has a first end 122 (distal end) and an opposing second end 124 (proximal end) and the second part 140 has a first end 142 (distal end) and an opposing second end 144 (proximal end). The first and second parts 120, 140 are coupled to one another in a rotational manner in that the more proximal second part 140 can rotate relative to the more distal first part 120. In particular, the first end 142 is rotationally coupled to the second end 124 of the first part 120.

In this embodiment, the more proximal second part 140 rotates relative to the outer tube 200, yet the more distal first part 120 does not and it only changes position in a longitudinal manner (e.g., in a longitudinal direction along the length of the needle). Accordingly, the longitudinal movement of the more distal first part 120 activates or deactivates the capturing mechanism, namely, the capturing mechanism 300. Since the capturing mechanism 300 is activated by a longitudinal translation which results in the geometry of the capturing mechanism 300 changing, the capturing mechanism 300 can be referred to as a translational coil or Tcoil. As mentioned above, this is in contrast to snare coils whose activation mechanisms are dependent on a rotational movement of the coil (these type of coils are disclosed in Applicant's previous applications and can be referred to as rotational coils or Rcoils). A snare coil is an example of an Rcoil.

Any number of different coupling schemes can be provided to allow the proximal element to rotate relative to the distal element while coupling/translating the longitudinal displacement of the proximal element to a longitudinal displacement of the distal element; however, in the illustrated embodiment, a rotating coupling 150 is provided. The coupling 150 is formed of a lip 127 that extends distally from the first end 142 of the second part 140 and the second end 124 of the first part 120 includes a complementary protrusion (tab) 149.

The protrusion 149 can thus be in the form of an annular flange that extends radially inward from the inner tube 120. Similarly, the lip 127 extends radially inward from the second part 140 of the inner tube and defines an L-shaped catch member that receives and engages the protrusion 149 to permit rotation of the second part 140 relative to the first part 120. To mate the two parts 120, 140 together, the protrusion 149 is inserted into the lip 127. This arrangement allows the proximal second part 140 to rotate relative to the distal first part 120 of the inner tube 110, while maintaining a connection between the proximal portion (second part 140) and the distal portion (first part 120) in order that a longitudinal motion of the more proximal second part 140 is converted into a longitudinal displacement of the distal portion (first part 120) of the inner tube 110.

The embodiment of FIG. 1 is only one example of a coupling 150 that achieves the goal of allowing the proximal second part 140 to rotate relative to the distal first part 120 yet translate longitudinal motion of the more proximal second part 140 to a longitudinal motion of the distal first part 120 of the inner tube 110. Another construction that facilitates the rotation of the proximal second part 140 relative to the distal first part 120 of the inner tube 110, while facilitating longitudinal translation of the inner tube 110 relative to the outer tube 200 is illustrated in FIG. 10.

Figure 10:
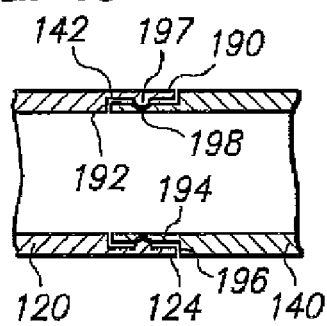
FIG. 10 is a partial cross-sectional view of a rotary coupling according to one embodiment.

The construction of FIG. 10 provides a more compact type of sleeve design in which the second end 124 of the distal first part 120 has a protrusion or sleeve 190 extending therefrom and having a thickness less than the thickness of the rest of the first part 120 so as to form an inner shoulder 192. The first end 142 of the proximal second part 140 has a complementary protrusion or sleeve 194 extending therefrom and having a thickness less than the thickness of the rest of the second part 140 to form an outer shoulder 196. Along an inner surface of the sleeve 190, a first coupling member 197 is formed and similarly, along an outer surface of the sleeve 194, a second coupling member 198 is formed. The sleeves 190, 194 have some resiliency and flexing action to permit mating between the two and in particular, to permit mating between the first and second coupling members 197, 198.

To couple the first and second parts 120, 140, the flange 190 is disposed exterior to and around the outer surface of the sleeve 194 and the two parts 120, 140 are moved toward one another until the first coupling member 197 mates with the second coupling member 198. In the illustrated embodiment, the first coupling member 197 is in the form of a protrusion, tab, etc., (e.g., annular protrusion) and the second coupling member 198 is in the form of a recess or channel (e.g., annular channel) that is sized to receive the first coupling member 197 so as to securely couple the two together and insure that longitudinal translation of the proximal second part 140 is converted into an equivalent longitudinal displacement of the distal first part 120 of the inner tube 110. In this manner, the first and second parts 120, 140 can snap fittingly and mate with one another. Other types of coupling member configurations can be incorporated into complementary sleeve designs to insure that longitudinal translation of the proximal second part 140 is converted into an equivalent longitudinal displacement of the distal first part 120 of the inner tube 110 while allowing the sleeve 192 to rotate relative to the sleeve 190. The complementary sleeve design achieves the goal of minimizing internal protrusions extending from the internal aspect of the inner tube 110 into the lumen of the inner tube which might obstruct the transition of a specimen within the internal collecting space of the inner tube.

The position of the rotational coupling of the inner tube 110 can be located more distally or more proximally along the length of the inner tube 110. A more distal location of the coupling can provide for a more compact type of coil/distal inner tube configuration facilitating the manufacture of the coil/distal inner tube component as a single unit. Also, there may be an advantage in some embodiments to have the coupling at a distal aspect especially in long needles in which a substantial length of the proximal portion 140 of the inner tube 110 is configured as a wire or solid tube which is used to transmit the longitudinal displacement. In that embodiment, the coil/distal tube configuration is in the form of a capturing/collecting module located at the distal aspect of a long needle as required for endoscopic or laparoscopic applications.

In accordance with one embodiment of the present invention, the proximal second part 140 includes a mechanism 230 that allows for the conversion of a rotation of the proximal second part 140 of the inner tube 110 into a longitudinal displacement. For example, one type of mechanism 230 is illustrated in FIG. 1 and is in the form of a groove or channel 240 formed in the second part 140 of the inner tube 110 and a complementary pin or protrusion 250 extending from the outer tube 200. The handle assembly of the needle 100 includes a lever 260 that is attached to the inner tube 110 and more specifically to the proximal second part 140. The lever 260 is disposed within a channel of the handle so that it can be rotated. Rotation of the second part 140 causes the pin 250 to travel along the groove 240 and because of the pitch of the groove 240, the rotation results in longitudinal motion of the proximal portion of the inner tube 140 relative to the outer tube 200 which is translated through the rotational coupling to the distal section of the inner tube 120, ultimately resulting in longitudinal motion of the whole inner tube 110 relative to the outer tube 200. The lever 260 can be connected to the inner tube 110 in any number of different ways and for example, the level 260 can be connected to the inner tube 110 with a pin 262 that is disposed within a longitudinal slot located within the inner tube 110 so that the lever 260 can transmit a rotational torque to the inner tube and still allow the inner tube 110 to longitudinally translate as the pin 262 moves within the slot.

FIG. 1 illustrates a construction that includes rotation of the proximal second part 140 and allows for incorporation of the rotating lever 260 in the handle of the needle 100 which can improve ease of use in certain applications and designs. However, there are other embodiments in which the most proximal portion (second part 140) of the inner tube 110 does not rotate relative to the outer tube 200. In other words, in another embodiment shown in FIG. 6, an inner tube 111 can be made of one component or part without dividing it into a proximal portion and a distal portion connected by a rotating coupling as shown in FIG. 1.

Figure 6:
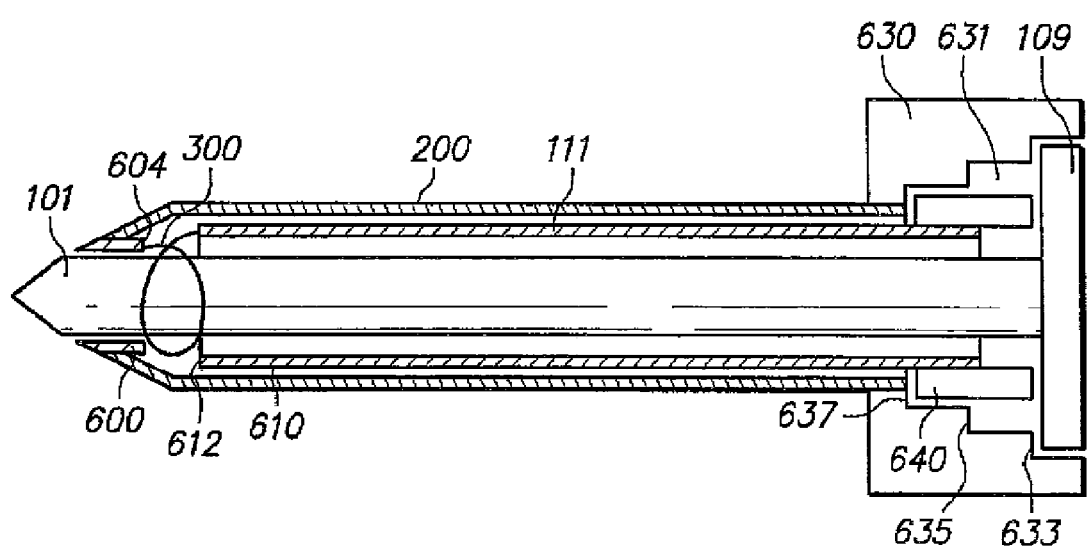
FIG. 6 is a cross-sectional view of a section of a biopsy needle in accordance with a sixth embodiment of the present invention.

In this embodiment, the inner tube 111 is translated longitudinally relative to the outer tube 200 by incorporating a variety of designs that provide for radial extensions of the inner tube 111 at its proximal aspect, 640 in FIG. 6 which allow for an operator or other mechanism to connect to the inner tube 110 and move it longitudinally relative to the outer tube 200. It will be appreciated that a simple longitudinal movement of the inner tube 111 or an inner wire will facilitate the application of the present technology to long or endoscopic tubes as described below. Also, such a configuration facilitates the design of automated needles in which a biasing or spring-loaded mechanism can be longitudinally fired in a proximal direction displacing the inner tube 111 proximally relative to the outer tube 200 and thereby, activating the distal capturing mechanism 300. This type of design eliminates the requirement for the pin and groove mechanism described above with reference to FIG. 1 to convert a longitudinal firing motion into a rotational motion of the inner tube 110 relative to the outer tube 200 which is required in Rcoil (snare coil) needles, and therefore, the Tcoil design is better suited for the development of automated full core biopsy needles.

Stylet 101 is included in the design to strengthen the tip of the needle 100 during penetration and localization of the needle adjacent to the region to be biopsied. Once the needle 100 is appropriately localized, the lumen of the needle 100 is opened by removing the stylet 101, providing a biopsy channel space for the specimen to enter as the needle is advanced. In automated designs, the inner and outer tube assembly is rapidly fired over and beyond the stylet 101 and the specimen enters the internal lumen of the inner tube 110 as a biopsy channel opens with the forward advancement of the needle assembly beyond the tip of the stylet 101.

Figure 2:
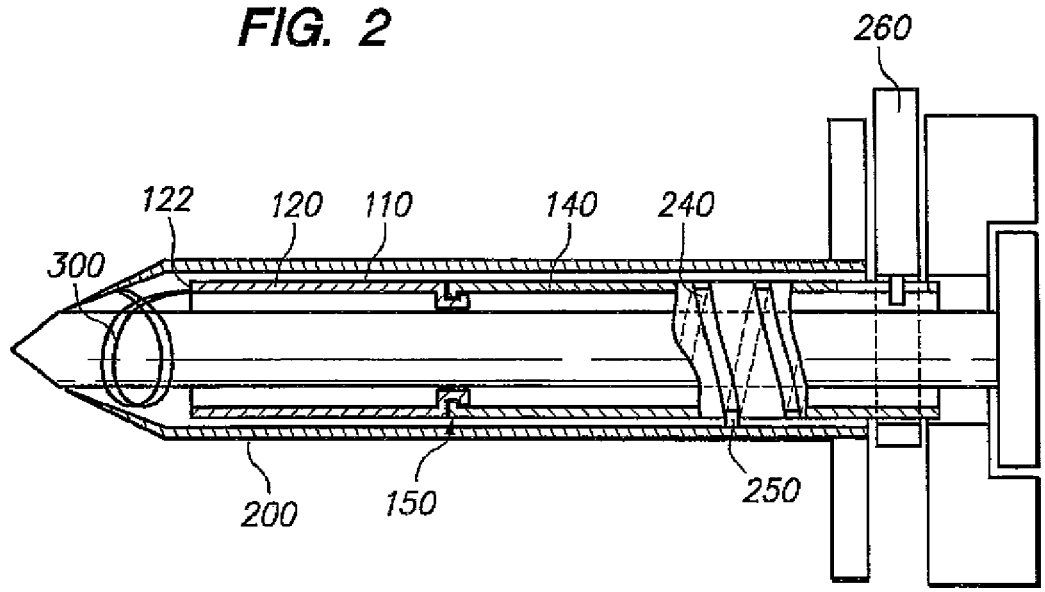
FIG. 2 is a cross-sectional view of a section of a biopsy needle in accordance with a second embodiment of the present invention.

In the embodiment of FIG. 1, the capturing mechanism 300 is illustrated as being a relatively delicate wire that has a longitudinal width providing the coil element 300 with some surface area which increases the area of engagement between the coil 300 and the material, and therefore facilitates the capturing or grabbing efficiency of the coil 300 relative to the specimen. The coil element 300 thus has a first end 302 that is coupled (attached) to the outer tube 200 and an opposite second end 304 that is coupled (attached) to the first end 122 of the distal first part 120. In the embodiment of FIG. 2 the capturing mechanism 300 is illustrated as a coil that has a more substantial longitudinal width providing the coil element 300 with an increased surface area, relative to a wire coil, which in turn further increases the area of engagement between the coil 300 and the biopsied material, and therefore facilitates the capturing or grabbing efficiency of the coil 300 relative to the specimen.

It will also be appreciated that the capturing mechanism 300 can be made of multiple coils that are configured in the same or opposite orientations (see Applicant's U.S. Pat. No. 745,645, which is hereby incorporated by reference in its entirety, also see FIG. 3). If a multitude of deformable elements are incorporated into the capturing mechanism 300, it can take the form of a capturing mesh as described in the U.S. Pat. No. 7,455,645.

Coils with opposite orientation can be incorporated into the capturing assembly since the capturing mechanism is activated by a longitudinal displacement of the capturing coils and not as a result of the application of a rotary motion or torque. Rotary motion of oppositely orientated coils will result in the decrease of the diameter of one coil and an increase in the diameter of the oppositely orientated coil while translational motion of oppositely orientated coils will result in the decrease of the diameters of all the coils and activation of the capturing mechanism, therefore increasing the applicability as well as the potential efficiency of multi-element Tcoil designs relative to such Rcoil configurations. Since oppositely orientated multicoil designs can be the basis for constructing diameter reducing mesh type capturing elements the Tcoil technology provides for the construction of such designs whereas the Rcoil technology does not.

Figure 3:
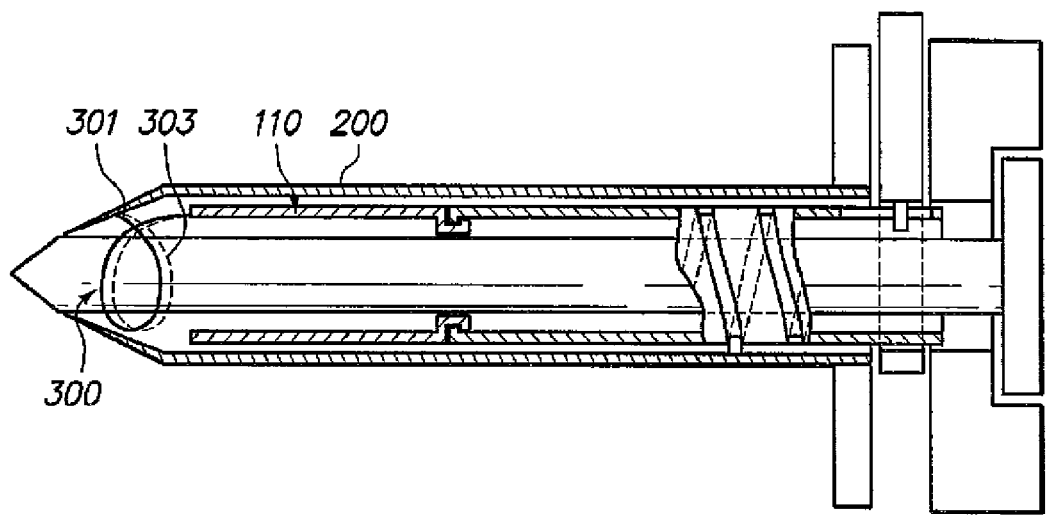
FIG. 3 is a cross-sectional view of a section of a biopsy needle in accordance with a third embodiment of the present invention.

FIG. 3 illustrates an embodiment in which two wire loops 301, 303 are configured and oriented to form the capturing mechanism. The second loop 303 is illustrated using a broken line only for purposes of illustration in order to more clearly differentiate the first loop 301 from the second loop 303 and not to indicate that the loop has interruptions along its length.

It will be understood that the capturing mechanism 300 must be in the form of a deformable member that is attached to the inner tube 110 and the outer tube 200 so that when the inner tube 110 is translated relative to the outer tube 200 longitudinally, the mechanism (wire, wires, strips or mesh) 300 deforms in a way se that it moves towards the central axis of the inner tube 110 or needle 100 itself. The proximal and distal portions of the deformable element or elements must have at least some angular displacement relative to the circumference of a circle defined by the distal portion of the inner tube 110 where the proximal portion of the deformable element (wire or wires) 300 is connected to the inner tube 110. In this way, some degree of curvature of the element 300 is elongated with longitudinal displacement of the capturing mechanism 300, and as a result, the element (or elements) 300 longitudinally "straightens" and seeks the central axis of the inner tube 110 (or needle 100), thereby capturing, snaring, or even severing the specimen.

Figure 4:
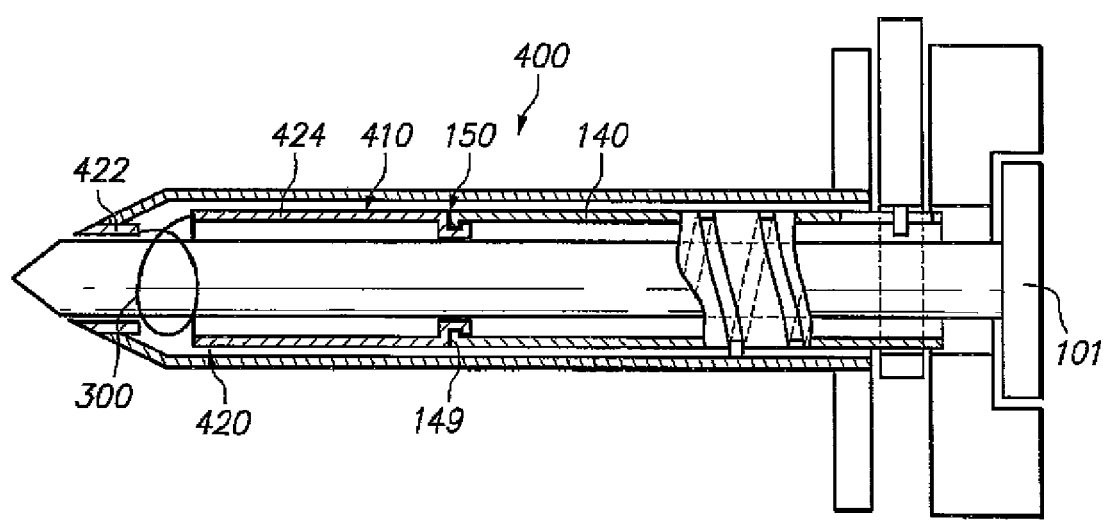
FIG. 4 is a cross-sectional view of a section of a biopsy needle in accordance with a fourth embodiment of the present invention.

As described in Applicant's previous snare coil patent applications, the inner tube 110 can have a distal portion located distal to the distal aspect of the coil 300 that can provide a type of tubular sleeve for incorporation into the tip structure. FIG. 4 illustrates a needle 400 that includes an inner tube 410 that is formed of the proximal second part 140 and a distal first part 420 that is coupled to the second part 140 with the coupling member 150. Unlike the embodiment of FIG. 1, the distal first part 420 has two sections, namely, a distal most first section 422 and a more proximal second section 424 that is closer to the second part 140. More specifically, the second section 424 includes the protrusion (tab) 149 but in this embodiment, the capturing element (e.g., wire) 300 is not directly attached to the outer tube 200 but instead is connected at its ends to the first section 422 and second section 424 of the first part 420. The first section 422 represents the distal most section of the inner tube 410 and the needle 400 for that matter since the first section 422 extends beyond a distal tip of the outer tube 200. The first section 422 is attached to the outer tube 200 using any number of different conventional techniques, including but not limited to welding or bonding techniques.

One end of the capturing element 300 is attached to the proximal end of the first section 422, while the other end of the capturing element 300 is attached to a distal end of the second section 424. In order for the distal tip of the needle 400 to have a smooth, continuous surface, the distal end of the first section 422 has a beveled construction that is complementary to the beveled nature of the outer tube 200. Since the first section 422 is in effect fixedly attached to the outer tube 200, the capturing element 300 is also fixedly attached to the outer tube 200.

To facilitate specimen transit through the tip and the coil 300 into the lumen of the inner tube 110 and needle itself 100, the application of increasing radial diameters that Applicant previously taught with respect to Rcoils is implemented with the present Tcoil constructions (see, Applicant's U.S. Pat. Nos. 7,338,456 and 7,384,400, each of which is hereby incorporated by reference in its entirety). Even though, the capturing mechanism 300 is not activated by a rotational motion as is the case with the capturing mechanism of the Applicants previously presented designs (see, Applicant's U.S. Pat. Nos. 7,338,456 and 7,384,400), the specimen must enter the needle 100 through the distal tip, pass through the coil 300 and then move into the lumen of the inner tube 110 if optimal specimen capture and retrieval is to be achieved. To facilitate specimen transit, the ratio of the diameter of the Tcoil to the diameter of the needle at the tip of the needle whether the tip is the distal most portion of the inner tube (FIG. 4) or of the distal portion of the outer tube 200 (FIG. 1) must be greater than 1. As described in the above referenced applications, the ratio can refer to a number of diameters; however, the numerator diameter always corresponds to a more proximal portion of the inner tube and the denominator diameter always represents a most distal portion of the inner tube with the ratio equal to greater than 1. In other words, there must be a step up in diameter to facilitate specimen transit and locating the step up closer to the tip of the needle increases the efficacy of specimen transit.

Figure 5:
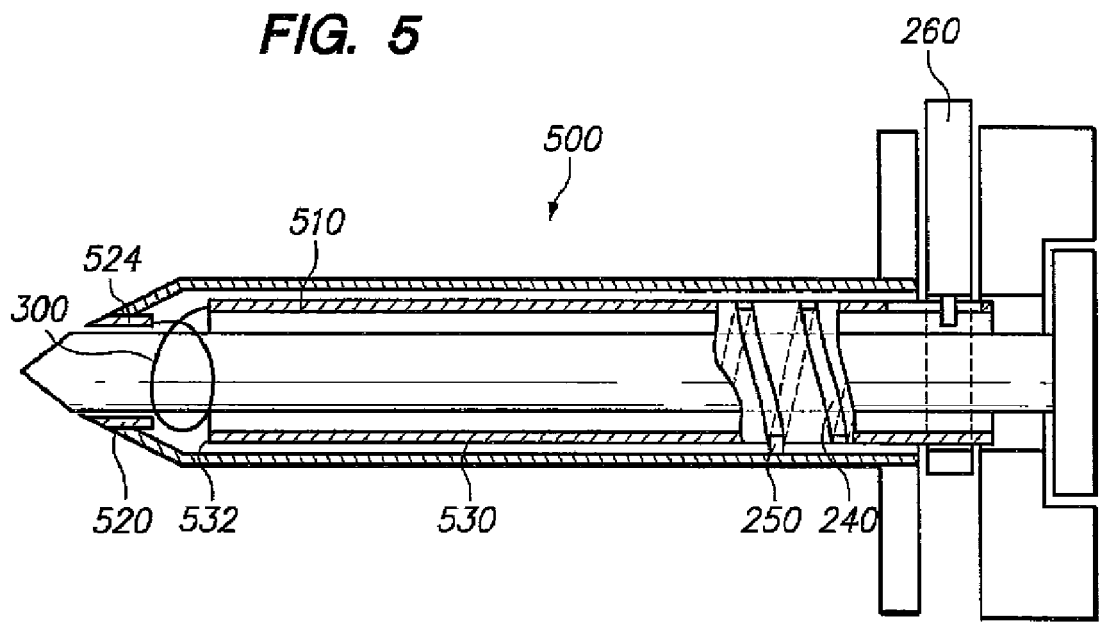
FIG. 5 is a cross-sectional view of a section of a biopsy needle in accordance with a fifth embodiment of the present invention.

FIG. 5 illustrates a needle 500 according to another embodiment. The needle 500 is of the type in which the rotating coupling element (member 150 in FIG. 1) has been removed. In this embodiment, an inner tube 510 does not have proximal and distal components connected by a rotatable coupling element. Therefore, rotation of the lever 260 results in rotation and longitudinal translation of the distal portion of the inner tube 510 and a rotational and translational decrease in the diameter of the capturing element 300.

In this embodiment, the inner tube 510 is formed of two parts, namely a more distal first part 520 and a more proximal second part 530. The second part 530 includes a distal end 532 that faces the first part 520 and the first part 520 has a proximal end 524 that faces the second part 530. In this embodiment, the capturing element (e.g., wire, coil or coils) 300 is not directly attached to the outer tube 200 but instead is connected at its ends to the first part 520 and the second part 530. The first part 520 represents the distal most section of the inner tube 510 and the needle 500 for that matter since the first part 520 extends beyond a distal tip of the outer tube 200. The first part 520 is attached to the outer tube 200 using any number of different conventional techniques, including but not limited to welding or bonding techniques. One end of the capturing element 300 is attached to the end 524 of the first part 520, while the other end of the capturing element 300 is attached to a distal end 532 of the second part 530. In order for the distal tip of the needle 500 to have a smooth, continuous surface, the distal end of the first part 520 has a beveled construction that is complementary to the beveled nature of the outer tube 200. Since the first part 520 is in effect fixedly attached to the outer tube 200, the capturing element 300 is also fixedly attached to the outer tube 200. However, other embodiments similar to the needle of FIG. 5 are possible, where the proximal portion of the inner tube does not consist of two parts connected by a rotationational coupling as in FIG. 1 and is a single non divided tube as in FIG. 5, and there is no distal inner tube element, 520. In such an embodiment, the distal portion of the coil is attached directly to the outer tube instead of a distal inner tube element, 520. The needle's tip is formed by the tip of the outer tube as opposed to the needle of FIG. 5 where the distal most portion of the inner tube represents the distal most portion of the needle or the needle's tip.

This embodiment incorporates a pin and groove mechanism in which the groove or channel 240 is formed in the second part 530 of the inner tube 510 and the complementary pin or protrusion 250 extends from the outer tube 200. The lever 260 is attached as described above with reference to the first embodiment. Rotation of the second part 530 causes the pin 250 to travel along the groove 240 and because of the pitch of the groove 240, the rotation results in longitudinal motion of the proximal portion of the inner tube 110, 530 relative to the outer tube 200. However, unlike a standard snare coil design, the pin and groove mechanism located in the proximal second part 530 of the inner tube 510 results in proximal longitudinal motion in addition to a rotational motion of the inner tube 510 relative to the outer tube 200. Therefore, the capturing mechanism 300 has the advantage of reducing its diameter both from a rotational conformational change, as well as a longitudinal conformational change, which results in an increase specimen capturing efficacy. It will be appreciated that the needle 500 neither depicts a simple Rcoil construction (snare coil) nor a Tcoil construction but rather a coil having rotational and translational deformability (i.e., an RTcoil).

The embodiment of FIG. 6 has been briefly described before and includes an inner tube 111 and similar to FIG. 5, the inner tube 111 is formed of two parts, namely a more distal first part 600 and a more proximal second part 610. The second part 610 includes a distal end 612 that faces the first part 600 and the first part 600 has a proximal end 604 that faces the second part 610. In this embodiment, the capturing element (e.g., wire, coil or coils) 300 is not directly attached to the outer tube 200 but instead is connected at its ends to the first part 600 and the second part 610. The first part 600 represents the distal most section of the inner tube 111 and the needle for that matter since the first part 600 extends beyond a distal tip of the outer tube 200. The first part 600 is attached to the outer tube 200 using any number of different conventional techniques, including but not limited to welding or bonding techniques. One end of the capturing element 300 is attached to the end 604 of the first part 600, while the other end of the capturing element 300 is attached to a distal end 612 of the second part 610. In order for the distal tip of the needle to have a smooth, continuous surface, the distal end of the first part 600 has a beveled construction that is complementary to the beveled nature of the outer tube 200. Since the first part 600 is in effect fixedly attached to the outer tube 200, the capturing element 300 is also fixedly attached to the outer tube 200. One end of the capturing element 300 is attached to the proximal end of the first part 600, while the other end of the capturing element 300 is attached to a distal end of the second part 610.

In the embodiment of FIG. 6, the lever 260 and rotating coupling mechanism 150 are eliminated. The coil/capturing mechanism 300 is activated through proximal translation/displacement of the inner tube relative to the handle 630 which results in increased longitudinal separation of the proximal and distal portions of the capturing coil 300 resulting in a decrease in the diameter of the capturing mechanism. More specifically, the stylet 101 includes a handle 109 to permit controlled movement of the stylet 101. The inner tube 111 includes handle 640 (which can be in the form of an annular flange extending around the proximal end of the second part 610.) The inner tube handle, 640 can be constructed of other elements located at the proximal portion of 610 so long as they allow a secure interaction with the tube to facilitate proximal displacement of the inner tube relative to the outer tube. These other elements can be designed to increase the radial diameter of the proximal portion of the proximal segment 610 of the inner tube to allow improved interaction with another mechanical element or an operator's hand. Alternatively it can be a constructed of coupling component(s) to allow interaction with a biasing mechanism for automated proximal displacements of the inner tube relative to the outer tube. The handle 630 of the needle includes a recessed cavity 631 in which the inner tube 111 and the stylet 101 are inserted. In the illustrated embodiment, the recessed cavity 631 has stepped constructions, with the steps defining and limiting the degree of travel of the stylet 101 and the inner tube 111. For example, the cavity 631 can include a first step 633 that limits the longitudinal distal insertion of the stylet 101 since the dimensions of the handle of the stylet 101 are greater than the dimensions of the inner diameter of the step 633. Similarly, the cavity 631 can include a second step 635 and a third step 637. The dimensions of the inner diameters of the second and third steps 635, 637 are such that the handle 640 can pass through the opening in steps 633, 635; however, the third step 637 restricts the forward motion of the handle 640 and thus, of the inner tube 111. Of course, the inner tube 111 and in particular, the second part 610 can be pulled rearwardly out of the handle of the needle.

Figure 7:
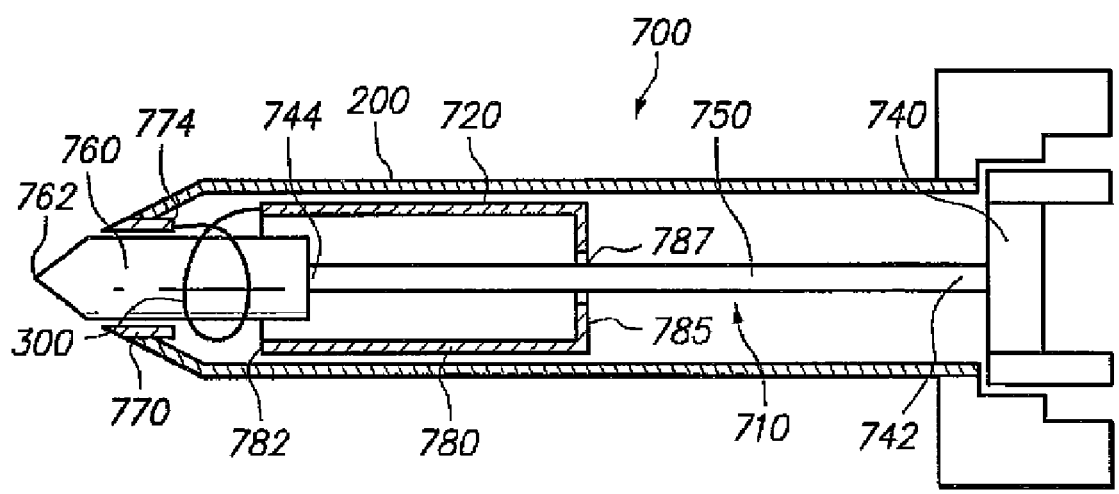
FIG. 7 is a cross-sectional view of a section of a biopsy needle in accordance with a seventh embodiment of the present invention.

FIG. 7 illustrates a needle 700 in which longitudinal translation is accomplished in a manner different than the other embodiments. In particular, the needle 700 includes the outer tube 200 that surrounds an inner tube 720 that is part of an inner stylet mechanism 710. The mechanism 710 has a displaceable handle 740 that is attached to a proximal end 742 of an elongated, displaceable connector member 750. The connector member 750 has an opposite distal end 744 and can be in the form of a wire or solid tube (e.g., an elongated dowel member). The distal end 744 of the connector member 750 is connected to and/or is integrally formed with a pointed stylet component 760. The connector member 750 is thus an intermediate member between the pointed stylet component 760 and the handle 740. The stylet component 760 thus has a pointed end 762. The handle 740 can be annular shaped and dimensioned to be received within a cavity formed in the regular handle on the needle. Alternatively it can be constructed of coupling component(s) to allow interaction with a biasing mechanism for automated longitudinal displacements of the inner tube relative to the outer tube.

The inner tube 720 is disposed within the outer tube 200 and is actually formed of two sections, namely, a distal first part 770 and a more proximal second part 780. The second part 780 includes a distal end 782 that faces the first part 770 and the first part 770 has a proximal end 774 that faces the second part 780. In this embodiment, the capturing element (e.g., wire, coil or coils) 300 is not directly attached to the outer tube 200 but instead is connected at its ends to the first part 770 and the second part 780. The first part 770 represents the distal most section of the inner tube 720 and the needle for that matter since the first part 770 extends beyond a distal tip of the outer tube 200. The first part 770 is attached to the outer tube 200 using any number of different conventional techniques, including but not limited to welding or bonding techniques. One end of the capturing element 300 is attached to the end 774 of the first part 770, while the other end of the capturing element 300 is attached to a distal end 782 of the second part 780. However, other embodiments similar to the needle of FIG. 7 are possible, where there is no distal inner tube element, 770. In such an embodiment, the distal portion of the coil is attached directly to the outer tube instead of a distal inner tube element, 770. The needle's tip is formed by the tip of the outer tube as opposed to the needle of FIG. 7 where the distal most portion of the inner tube represents the distal most portion of the needle or the needle's tip.

Unlike the previous embodiment, a proximal end 785 of the second part 780 is a substantially closed end; however, the end 785 has an opening 787 formed therein. The opening 787 is sized so that the connector member 750 can extend therethrough and can be longitudinally displaced therein. While the dimensions of the opening 787 and connector member 750 are complementary, the dimensions of the stylet component 760 are not complementary in that the stylet component 760 has a greater diameter and therefore, is unable to pass through the opening 787. The open distal end 782 of the second part 780 is sized so that the stylet component 760 can be received completely therein into the interior of the second part 780. When the capturing element 300 is in the relaxed position shown in FIG. 7, its loop(s) is/are large enough that the stylet component 760 can pass therethrough.

The needle 700 is particularly suited to a long needle configuration, such as those required for laparoscopic or endoscopic biopsy techniques. The connector component 750 passes through opening 787 at the proximal portion of the inner tube 720 allowing the stylet to be displaced proximally without displacing the inner tube 720 until a proximal portion of the stylet component 760 comes into contact with the proximal portion (end 785) of the second part 780. As the diameter of the stylet component 760 is greater than a diameter of the opening 787 in the proximal portion of the second part 780 further longitudinal displacement of the connector component 750 in the proximal direction toward the handle of the needle causes the second part 780 of the inner tube 720 to be displaced proximally and therefore allows activation of the coil or capturing mechanism 300 as the distance between the distal and proximal aspect of the capturing mechanism 300 increases as the inner tube component is longitudinally displaced proximally.

As depicted in FIG. 7, certain needle designs call for or require long extensions of the needle assembly to allow for biopsy at a point located a significant distance from the needle's handle, especially in laparoscopic or endoscopic applications. The distal portion of the needle and coil/capturing mechanism can be activated through the use of less bulky inner tube designs including solid inner tubes with diameters substantially less than the inner diameter of the outer tube, or thick wires, either of which are attached to a distal stylet configuration. A relatively short inner tube is located at the distal portion of the outer tube 200 and is connected to the outer tube 200 through the capturing mechanism or coil 300 which is connected to the distal portion of the inner tube 720 at its proximal portion and to the outer tube at its distal aspect. The proximal aspect of the inner tube 720, 785 is located in the distal portion of the outer tube 200 and therefore, is not located adjacent to and is not directly connected to the proximal portion of the outer tube or the handle. The proximal portion of the inner tube 720 has an opening through which the solid tube or wire 750 passes and connects to the pointed stylet member 760.

In addition, there are a number embodiments that are possible to facilitate maintaining a closed off needle tip with a stylet member during needle insertion, opening the lumen of the needle/inner tube for specimen acquisition, activation of the translating capturing mechanism and subsequent specimen retrieval, using the distal shortened inner tube configuration. Two embodiments incorporating these elements are illustrated in FIGS. 8 and 9.

FIG. 8 illustrates a needle configuration 800 that can be used for capturing specimens with a Tcoil or translating coil at the end of a long endoscopic or laparoscopic needle. The needle 800 has four main components including a truncated (short) inner tube 810, a translating coil (or coils) 820 made of a material with memory, a stylet 850 and a connector member (e.g., thick wire or solid tube element) 840. The inner tube 810 has a proximal end 812 with an opening 813 formed therein through which the connector member 840 passes. A distal end of the connector member 840 connects with the stylet member 850 which has a diameter greater than the connector member 840 and which allows the opening at the tip of the needle, formed by the outer tube 200 to be closed off during needle penetration as shown in FIG. 8a.

Figure 8A:
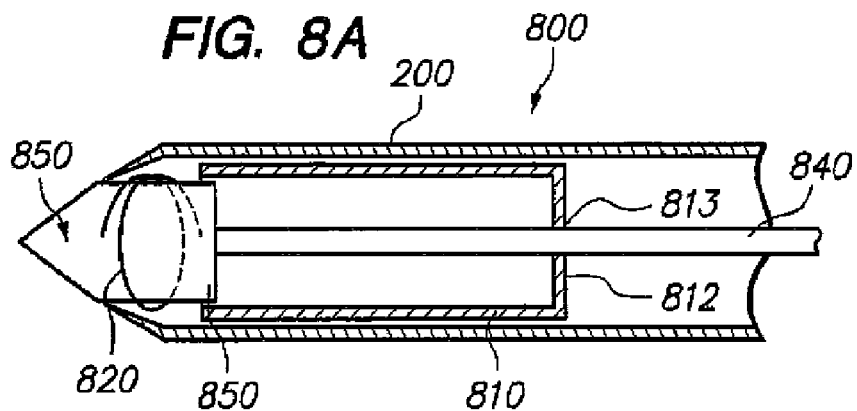
FIGS. 8a-f are cross-sectional views of a section of a biopsy needle in accordance with an eighth embodiment of the present invention showing the activation, capture and release of a specimen.
Figure 8B:
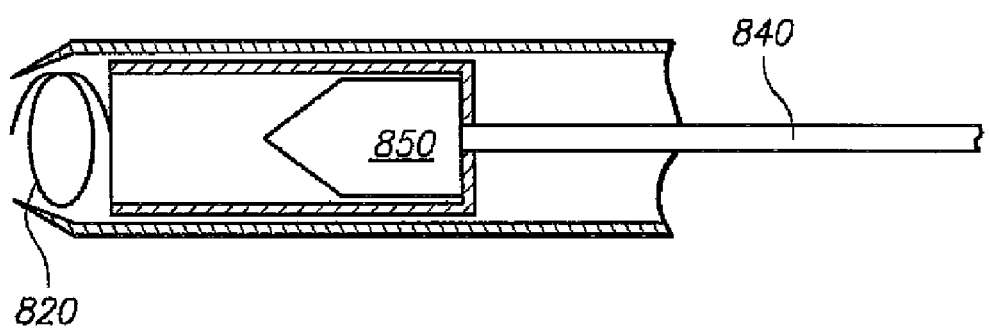
Figure 8C:
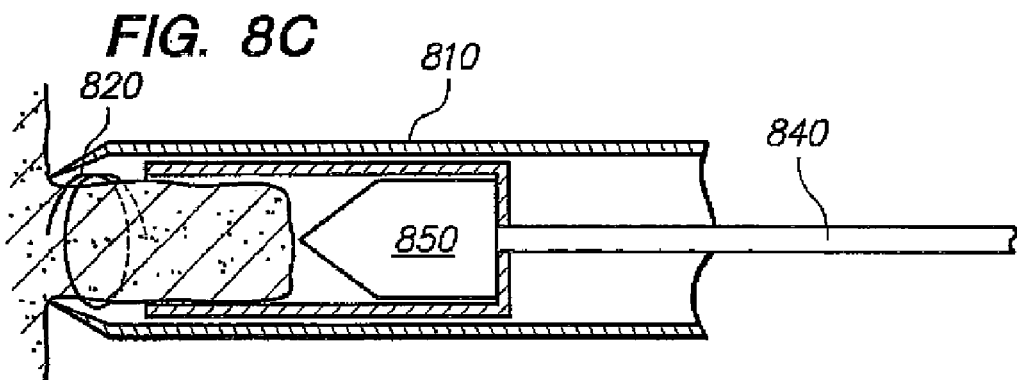
Figure 8D:
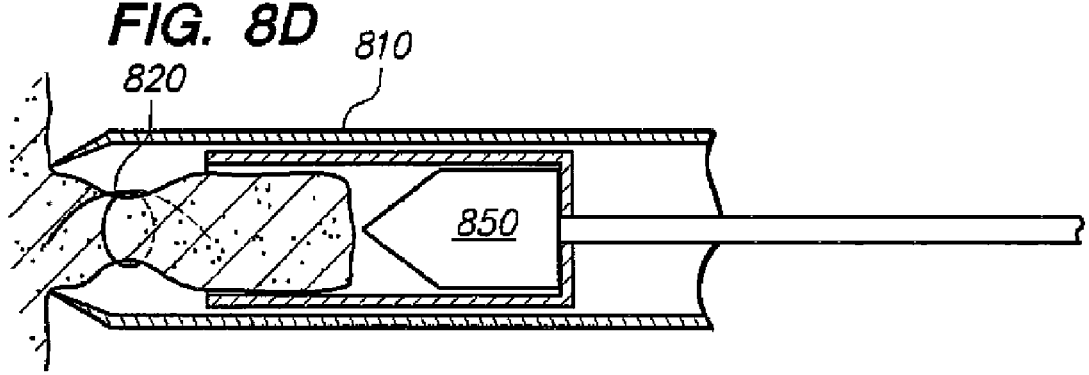
Figure 8E:
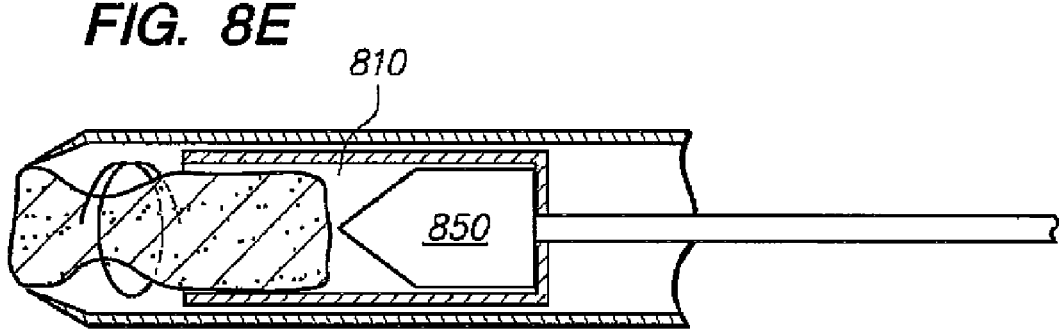
Figure 8F:
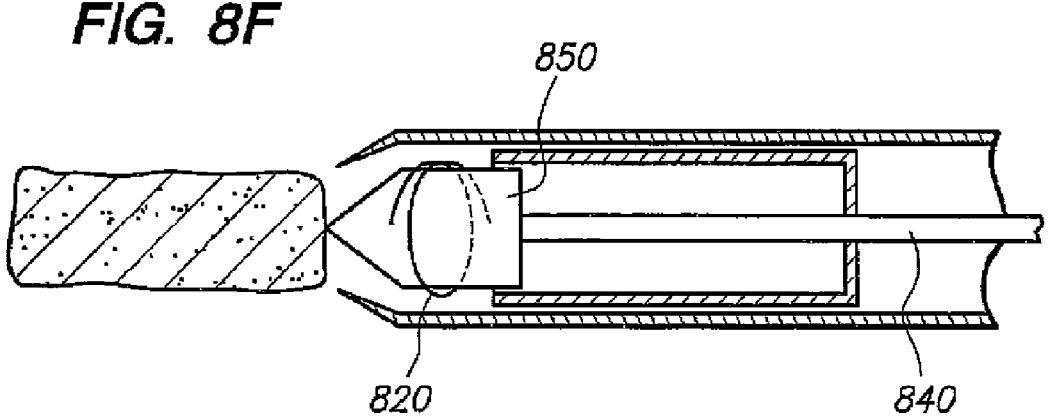

Once the needle 800 has been inserted into a tissue region to be biopsied, the connector member 840 is moved proximally and as the stylet member 850 is attached to the connector member 840, the stylet 850 is translated to the proximal portion of the inner tube 810. Displacement of the stylet member 850 proximally therefore opens up the tip formed by the outer tube 200 allowing movement of the specimen into the lumen of the inner tube 810 through the coil 820. It will be appreciated that the outer tube 200 is not illustrated in FIGS. 8(b)-(f) only for purposes of simplicity and clarity; however, the outer tube 200 would be positioned as it is shown in FIG. 8a, i.e., surrounding the inner tube 810, etc. in a fully manufactured needle and therefore is not drawn but implicitly included in FIGS. 8(b)-(f). Once the tip of the needle 800 is open and the lumen of the inner tube 810 is available to receive a specimen, the needle assembly, 800/outer tube, 200 is moved forward and as it projects forward, a tissue specimen or core passes through the tip of the needle past the coil 820 and into the inner aspect or luminal space of the inner tube 810 for collection as shown in FIG. 8c. Since the proximal portion of the stylet member 850 has a greater diameter than the opening 813 in the proximal portion 812 of the inner tube 810, displacing the connector member 840 further proximally results in the inner tube 810 being displaced further proximally, thereby activating the translational coil 820 as demonstrated by the decrease in the diameter of the capturing coil 820 as shown in FIG. 8d. Since according to one embodiment, the capturing coil 820 is made of a material that has memory, such as Nitinol, once the connector member 840 is displaced distally, disengaging the proximal portion of the stylet member from the proximal aspect of the inner tube 810, the inner tube assembly can move more distally and by a translational displacement, the capturing coil 820 can resume its original configuration and reverts to a greater diameter as shown in FIG. 8e. After the capturing coil 820 increases its diameter by resuming its original configuration, the stylet can be displaced distally by displacing the connector member 840 more distally and the specimen can be recovered for processing and analysis as shown in FIG. 8f.

FIGS. 9a-e illustrate a needle 900 that includes a truncated inner tube configuration that is adapted for use for long endoscopic or laparoscopic needles that do not require a capturing coil that has memory but incorporates somewhat more complex mechanics and design. As in the embodiment of FIG. 8, the outer tube 200 is shown only in FIG. 9a; however, the outer tube 200 has been eliminated in FIGS. 9b-9e for clarity and would normally be part of the fully manufactured needle and therefore is not drawn but implicitly included in FIGS. 9(b)-(e). The needle 900 includes an inner tube 910 that includes a proximal portion 912 that has an opening 913 formed therethrough.

Instead of one connector member 901 connecting directly to a stylet member 930, there are two additional components between the connector 901 and stylet 930. Immediately distal to the end of the connector member 901 is another element 940 that can have a cylindrical/elongated shape but includes an asymmetric component 942 about its periphery (also, see FIG. 9e). Distal to the asymmetric cylindrical component 942 is an element that also can be cylindrical, section 944, which connects the distal portion of the asymmetric component 942 to the proximal portion of the stylet member 930. The connecting element 944 between the stylet member 930 and the asymmetric component 942 has a diameter that is less than the diameter of the asymmetric member 942 and stylet 930. Also, the overall diameter of the asymmetric element 942 is less than the diameter of the stylet 930. Located in the proximal portion of an inner tube 910 is the opening 913 which is also asymmetric but complementary to the configuration of the asymmetric cylindrical component 942.

Figure 9A:
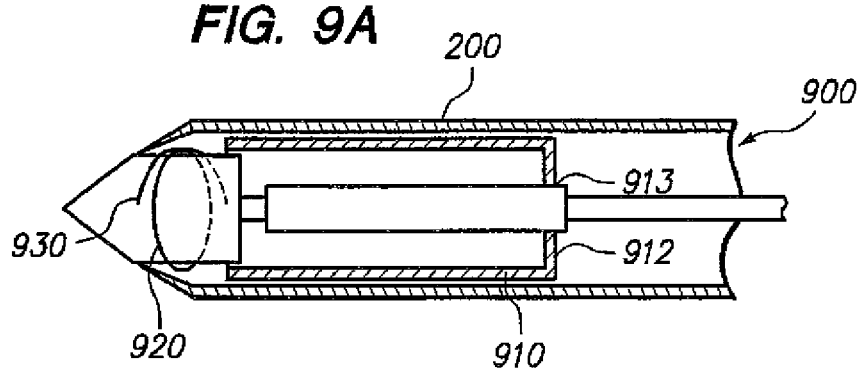
FIGS. 9a-e are cross-sectional views of a section of a biopsy needle in accordance with an ninth embodiment of the present invention showing the activation, capture and release of a specimen.
Figure 9B:
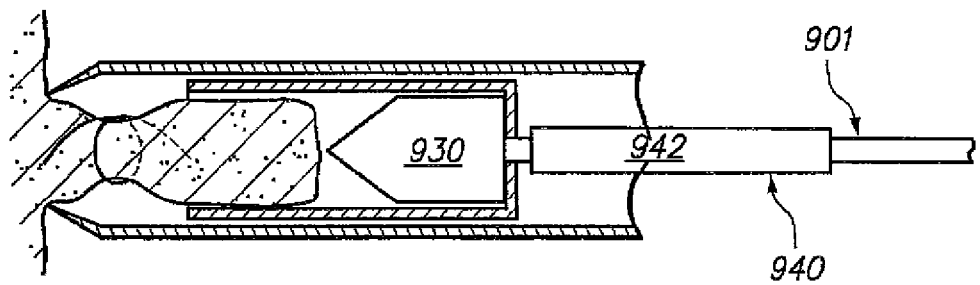

As shown in FIG. 9a, the stylet 930 is positioned to close off the opening at the end of the needle 900 formed by the outer tube 200. In FIG. 9b, the connector member 901 (e.g., wire or solid tube) is displaced proximally resulting in the lumen of the inner tube 910 being opened. The outer tube 200 has been projected forward, distally, the specimen material has entered the lumen of the inner tube 200, and the inner tube 910 has been displaced further proximally as the greater diameter of the stylet 930 has caused further proximal displacement of the connector member 901 to proximally displace the inner tube 910. Proximal displacement of the inner tube 910 has activated the coil 920 so that its diameter has decreased.

Figure 9C:
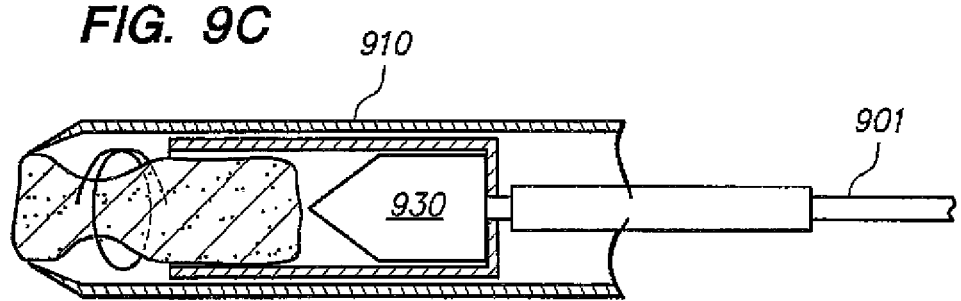
Figure 9D:
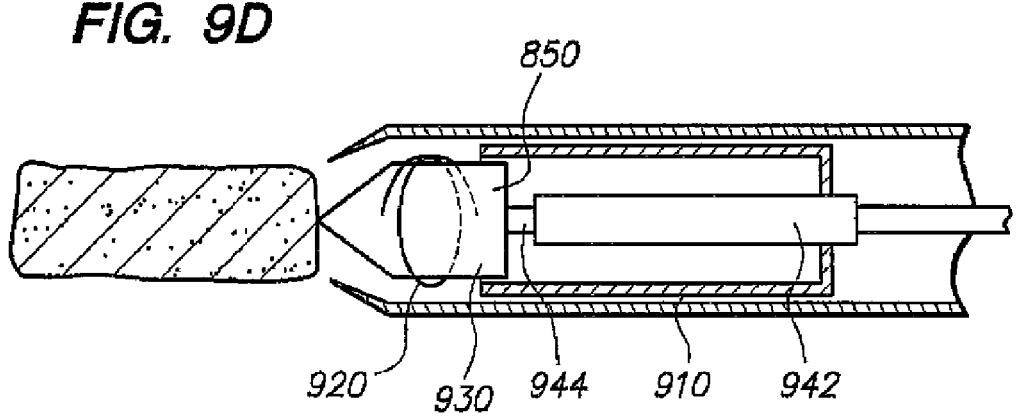
Figure 9E:
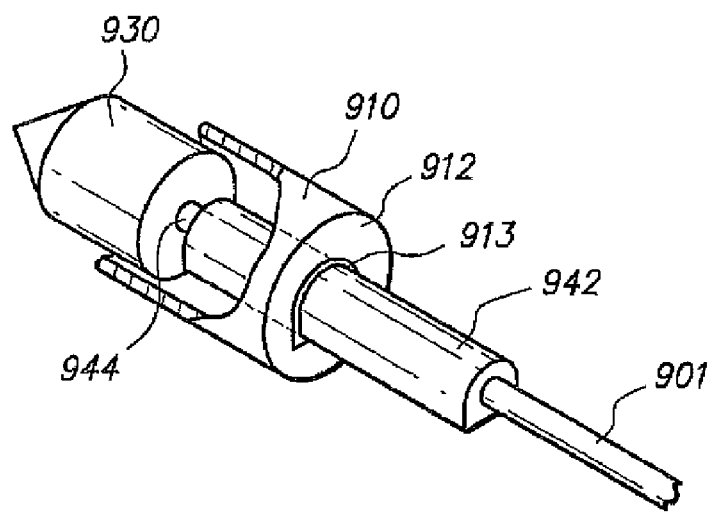

In FIG. 9c, the connector member 901 is rotated on its longitudinal axis so that the asymmetrical cylinder 942 can not pass through its complementary opening 913 formed in the proximal portion 912 of the inner tube 910. Therefore, as the connector member 901 is distally displaced, the inner tube 910 is distally displaced, increasing the diameter of the capturing element 920, thereby freeing the specimen for removal as shown in FIG. 9c. The connector member 901 is then rotated again so that the asymmetric cylinder 942 is again aligned with the complementary opening 913 in the proximal portion 912 of the inner tube 910 and can pass through the proximal portion 912 as it is advanced distally thereby displacing the stylet 930 distally and allowing the specimen to be displaced and removed from the inner lumen of the inner tube 910 as shown in FIG. 9d.

Although the previous embodiments incorporate a design where the inner tube or a solid tube is displaced proximally to activate the capturing or translating coil, other designs are possible where the inner tube or solid tube is displaced distally, causing a capturing element or elements to deformably decrease its diameter, thereby holding or capturing a specimen for removal. Once the needle is removed, the specimen can be recovered by displacing the inner tube or solid tube proximally increasing the diameter of the capturing element or elements and opening it for retrieval of the specimen. Distal longitudinal displacement of the translational coils can result in a reduction of the coil or capturing mechanism diameter and the reductions in the diameter can cause the specimen to be severed.

Figure 11A:
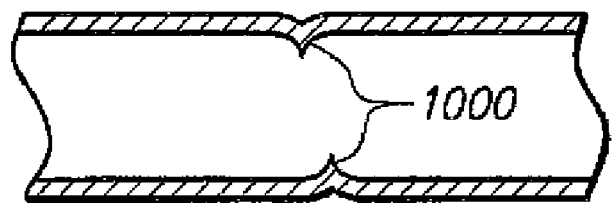
FIGS. 11a-c are cross-sectional views of a collapsible translational coil according to one embodiment.
Figure 11B:
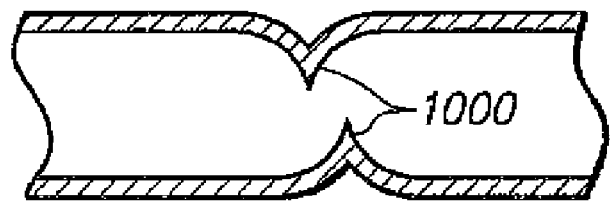
Figure 11C:
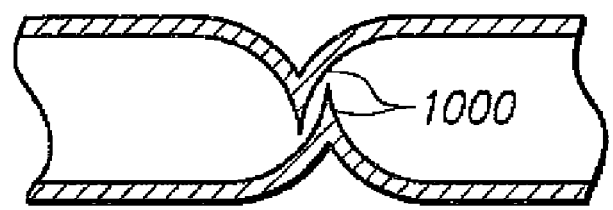

FIG. 11 illustrates an embodiment in which two spikes or protrusions 1000 exist as part of the collapsible translational coil. Other embodiments with more than two spikes or protrusions are possible. The coil is formed of a resilient deformable material and is designed so that as the coil is displaced distally, the height of the spikes 1000 increases. As the pinnacle of each protrusion 1000 is pointedly shaped and one protrusion 1000 is displaced slightly longitudinally relative to the other protrusion 1000, as the diameter of the capturing mechanism reduces, the pinnacles of the protrusions 1000 approach each other and become a cutting mechanism for severing a specimen. Capturing elements with more blunt spikes 1000 can simply grab the specimen for recovery.

Additionally, it is possible to configure Tcoils that are designed for proximal translational activation from coils or wire elements with sharp edges that would facilitate severing a specimen from a tissue as well as securing it for subsequent retrieval.

While the embodiments shown and described above are fully capable of achieving the objects and advantages of the present invention, it is to be understood that these embodiments are shown and described solely for the purposes of illustration and not for limitation.

What is claimed is:

1. A biopsy needle for removal of tissue comprising:
   an outer tube having a distal end and an opposing proximal end;
   an inner tube at least partially disposed within said outer tube; and
   a mechanism that has a variable diameter for capturing a tissue specimen, the mechanism including a distal end that is directly fixed to the outer tube and an opposing proximal end that is directly attached to the inner tube, the mechanism being entirely contained within the outer tube;
   wherein at least a portion of the inner tube is free to move longitudinally within and relative to the outer tube, whereby longitudinal movement of the moveable portion of the inner tube relative to the outer tube causes activation of the mechanism for capturing and releasing, respectively, the specimen, wherein longitudinal movement in a proximal direction away from the distal end of the outer tube towards the proximal end of the outer tube causes a reduction in the diameter of the mechanism for capturing the specimen.

2. The needle of claim 1, wherein the mechanism is a coil and the distal end of the coil is directly fixed to the outer tube and the proximal end of the coil is directly attached to a distal end of the inner tube.

3. The needle of claim 1, wherein the inner tube includes a first proximal part and a second distal part that are coupled to one another such that the first proximal part can rotate relative to the second distal part, while maintaining a coupling between the two so that longitudinal motion of the first proximal part is converted into a longitudinal displacement of the second distal part of the inner tube, thereby activating the mechanism.

4. The needle of claim 3, wherein one of the first proximal part and the outer tube includes a groove and the other of the first proximal part and the outer tube includes a complementary pin that is received within the groove, the groove having a pitch so that rotation of the first proximal part results in the pin traveling within the groove causing the inner tube to move longitudinally relative to the outer tube resulting in activation of the mechanism.

5. The needle of claim 4, wherein the first proximal part of the inner tube is coupled to a lever that can be rotated within a slot formed in a handle of the needle, the rotation of the lever transmitting a rotational torque to the inner tube while permitting the inner tube to longitudinally translate as the pin travels within the groove.

6. The needle of claim 5, wherein the lever is connected to the inner tube with a pin that is disposed within a longitudinal slot that is formed in the inner tube.

7. The needle of claim 1, wherein the mechanism includes a plurality of coils.

8. The needle of claim 1, wherein the mechanism is a coil and has a portion that has first inner diameter ($ID_{first}$) and a more distal portion of the needle that includes the distal end of the needle has a second inner diameter ($ID_{second}$), with a ratio $(R)=(ID_{first})/(ID_{second})$ that is greater than 1.

9. The needle of claim 8, wherein R is greater than 1.15, 1.20, 1.25, 1.30, or 1.35.

10. The needle of claim 1, wherein a proximal portion of the inner tube has a first inner diameter ($ID_{first}$) and a distal portion of the inner tube has a second inner diameter ($ID_{second}$), with a ratio $(R)=(ID_{first})/(ID_{second})$ that is greater than 1.

11. The needle of claim 1, wherein the inner tube includes a proximal part and a distal part, the distal part of the inner tube extending beyond the distal end of the outer tube so as to define a distal tip of the needle, the distal part being fixedly connected to the outer tube, the proximal part being operably connected to an actuator to permit the proximal part to move longitudinally within the outer tube, thereby activating the capturing mechanism.

12. The needle of claim 11, wherein the capturing mechanism comprises a coil and the distal end thereof is directly fixed to the distal part of the inner tube and the proximal end thereof is directly attached to a distal end of the proximal part of the inner tube.

13. The needle of claim 12, wherein one of the proximal part and the outer tube includes a groove and the other of the proximal part and the outer tube includes a complementary pin that is received within the groove, the groove having a pitch so that rotation of the proximal part results in the pin traveling within the groove causing the proximal part of the inner tube to move longitudinally relative to the outer tube resulting in activation of the mechanism.

14. The needle of claim 1, wherein a proximal end of the inner tube has an opening formed therethrough and a stylet for use with the needle, the stylet including a handle, a connector element that has a first end that is connected to the handle and a second end that is connected to a stylet member that has a pointed end, the connector element being sized to freely move in a longitudinal direction within the opening; however, the stylet member has dimensions greater than the opening and therefore, the stylet member is prevented from passing. therethrough.

15. The needle of claim 14, wherein the handle and connector are free to move in the proximal direction to cause activation of the mechanism.

16. A biopsy needle for removal of tissue comprising:
an outer tube having a distal end;
an inner tube at least partially disposed within said outer tube; and a mechanism that has a variable diameter for capturing a tissue specimen, the mechanism comprising a coil that has a distal end and a proximal end;
wherein at least a portion of the inner tube is free to move longitudinally within and relative to the outer tube, whereby longitudinal movement of the moveable portion of the inner tube causes activation of the mechanism for capturing and releasing, respectively, the specimen, wherein the inner tube includes a first proximal part, a second intermediate part and a third distal part, the first proximal part and second intermediate part being coupled to one another such that the first proximal part can rotate relative to the second intermediate part, while maintaining a coupling between the first proximal part and the second intermediate part so that longitudinal motion of the first proximal part is converted into a longitudinal displacement of the second intermediate part of the inner tube, thereby activating the mechanism, the third distal part of the inner tube extending beyond a distal end of the outer tube and being coupled thereto so as to define a distal tip of the needle, the distal end of the coil being directly attached to the third distal part of the inner tube and the proximal end of the coil being directly attached to a distal end of the second intermediate part of the inner tube.

17. The needle of claim 16, wherein one of the first proximal part and the outer tube includes a groove and the other of the first proximal part and the outer tube includes a complementary pin that is received within the groove, the groove having a pitch so that rotation of the first proximal part results in the pin traveling within the groove causing the first proximal part and second intermediate part of the inner tube to move longitudinally relative to the outer tube resulting in activation of the mechanism.

18. A biopsy needle for removal of tissue from a patient comprising:
an outer tube;
an inner tube disposed within and movable in a longitudinal direction relative to the outer tube; and a specimen capturing member that has a variable diameter for capturing a tissue specimen, the capturing member being directly coupled at a first end to a fixed structure that is different from the inner tube and is located within the outer tube, the specimen capturing member being directly coupled at a second end to the inner tube, wherein the specimen capturing member is entirely contained within the outer tube;
wherein longitudinal movement of the inner tube relative to the outer tube causes activation of the specimen capturing member resulting in the closing and opening, respectively, of the specimen capturing member to capture and release the specimen, respectively.

19. A method for removal of tissue from a patient comprising the steps of:
providing a biopsy needle including:
an outer tube having a distal end;
an inner tube at least partially disposed within said outer tube, wherein at least a portion of the inner tube is free to move longitudinally within the outer tube; and
a capturing mechanism that has a variable diameter for capturing a tissue specimen, the capturing mechanism including a distal end that is fixed relative to the distal end of the outer tube and an opposing proximal end that is attached to the inner tube, wherein the capturing mechanism is contained entirely within the outer tube; and
longitudinally moving the moveable portion of the inner tube relative to the outer tube and in a direction away from the distal end of the outer tube to activate the capturing mechanism resulting in the closing of the capturing mechanism to capture the specimen, wherein longitudinal movement of the movable portion of the inner tube in an opposite direction toward the distal end of the outer tube causes the capturing mechanism to open, thereby releasing the specimen.

20. The method of claim 19, wherein the step of longitudinally moving the inner tube to activate the capturing mechanism comprises the step of:
rotating a proximal part of the inner tube that causes a distal part of the inner tube to move longitudinally, thereby activating the capturing mechanism that is attached to the distal part, the proximal part being rotatably coupled to the distal part.

21. The method of claim 20, wherein the step of rotating the proximal part comprises the step of causing a pin associated with one of the proximal part and the outer tube to ride within a complementary groove associated with the other of the proximal part and the outer tube.

22. The method of claim 19, wherein the capturing member comprises a coil that is fixed at a distal end directly to the outer tube and is attached at a proximal end directly to the inner tube.

23. The method of claim 19, wherein the inner tube includes a proximal part and a distal part, the distal part of the inner tube extending beyond the distal end of the outer tube so as to define a distal tip of the needle, the distal part being fixedly connected to the outer tube, the proximal part being operably connected to an actuator to permit the proximal part to move longitudinally within the outer tube, thereby activating the capturing mechanism, the capturing mechanism being attached to and between the proximal part and distal part.

* * * * *